US008110386B2

(12) United States Patent
Suzuki et al.

(10) Patent No.: US 8,110,386 B2
(45) Date of Patent: Feb. 7, 2012

(54) LIPASE POWDER, METHODS FOR PRODUCING THE SAME AND USE THEREOF

(75) Inventors: Junko Suzuki, Yokosuka (JP); Satoshi Negishi, Yokosuka (JP); Yuri Arai, Yokosuka (JP); Chika Sakurai, Yokosuka (JP)

(73) Assignee: The Nisshin Oillio Group, Ltd., Tokyo (JP)

( * ) Notice: Subject to any disclaimer, the term of this patent is extended or adjusted under 35 U.S.C. 154(b) by 69 days.

(21) Appl. No.: 12/314,473

(22) Filed: Dec. 11, 2008

(65) Prior Publication Data

US 2009/0104680 A1 Apr. 23, 2009

Related U.S. Application Data

(60) Division of application No. 11/320,756, filed on Dec. 30, 2005, now abandoned, which is a continuation of application No. PCT/JP2005/006908, filed on Apr. 8, 2005.

(30) Foreign Application Priority Data

Apr. 8, 2004 (JP) .................................. 2004-114443

(51) Int. Cl.
*C12N 9/96* (2006.01)
(52) U.S. Cl. ....... 435/188; 435/134; 435/198; 424/94.3; 424/94.6
(58) Field of Classification Search .................. 435/188, 435/134, 198; 424/94.3, 94.6
See application file for complete search history.

(56) References Cited

U.S. PATENT DOCUMENTS

| 4,766,074 | A | 8/1988 | Havera et al. |
| 4,798,793 | A | 1/1989 | Eigtved |
| 5,166,064 | A | 11/1992 | Usui et al. |
| 5,480,787 | A | 1/1996 | Negishi et al. |
| 6,030,821 | A | 2/2000 | Soeda et al. |
| 6,399,059 | B1 | 6/2002 | Minoshima et al. |
| 6,635,303 | B1 * | 10/2003 | Youcheff et al. .............. 426/588 |

FOREIGN PATENT DOCUMENTS

| DE | 26 38 089 A1 | 3/1978 |
| EP | 0 322 213 B1 | 4/1994 |
| GB | 1 546 328 | 5/1979 |
| JP | 54-017179 A | 2/1979 |
| JP | 60-98984 A | 6/1985 |
| JP | 61-202688 A | 9/1986 |
| JP | 1-262795 A | 10/1989 |
| JP | 2-138986 A | 5/1990 |
| JP | 3-61485 A | 3/1991 |
| JP | 5-244948 A | 9/1993 |
| JP | 7-79789 A | 3/1995 |
| JP | 8-187095 A | 7/1996 |
| JP | 2668187 B2 | 10/1997 |
| JP | 11-349491 A | 12/1999 |
| JP | 2000-106873 A | 4/2000 |
| JP | 2002-539782 A | 11/2002 |
| TW | 305880 | 5/1997 |
| WO | WO 96/11264 A1 | 4/1996 |
| WO | WO 00/56869 A2 | 9/2000 |

OTHER PUBLICATIONS

Marek et al. Biotechnology Lett. (1996) 18(10): 1155-1160.*
Lukacs et al. J. Clinical Microbiol. (2004) 42(11): 5400-5402.*
Elmhurst Dairy webpate http://www.elmhurstdairy.com/milk/milkmilk.html downloaded Jul. 31, 2010, 2 pages.*
Shamsuzzaman et al. J. Dairy Sci. (1987) 70: 746-751.*
"Contents of Milk, What makes Milk So Special" from the webpage avoidingmilkproteins.com/1.htm downloaded Sep. 15, 2011.*
English Translation of the Japanese Office Action issued Nov. 15, 2010 corresponding to Japanese Patent Application No. 2006-519482 submitted by Applicant Dec. 15, 2010.*
English Translation of the Taiwanese Office Action dated Jan. 19, 2011 corresponding to Patent Application No. 094111250, submitted by Applicant Apr. 12, 2011.*
Translation of Korean Office Action issued Sep. 29, 2011; translation provided by FLS. Inc. Nov. 2011.*
Eissa et al. (Livestock Research for Rural Development 22(8) (2010)) downloaded from ww.Irrd.org/Irrd22/8/eiss22137.html on Nov. 29, 2011, 10 pages.*
International Search Report issued in corresponding International Patent Application No. PCT/JP2005/006908, Jul. 26, 2005, Japanese Patent Office, JP.
European Search Report issued in corresponding European Patent Application No. 05 72 8493, May 9, 2007, Munich, DE.
Pencreac'h, Gaëlle, et al., "*An Ultraviolet Spectrophotometric Assay for Measuring Lipase Activity Using Long-Chain Triacyglycerols from Aleurites fordii Seeds*", Analytical Biochemistry, 2002, pp. 17-24, vol. 303, No. 1, Elsevier Science, USA.
Wu, Xiao Yan, et al., "*Purification and Partial Characterization of Rhizomucor miehei Lipase for Ester Synthesis*", Applied Biochemistry and Biotechnology, 1996, vol. 59, No. 2, Humana Press Inc., USA.
Chen, L., et al., "*Detection and impact of protease and lipase activities in milk and milk powders*", International Dairy Journal, 2003, pp. 255-275, vol. 13, No. 4, Elsevier Science Ltd., Amsterdam, NL.
Sharma, Rohit, et al., "*Production, purification, characterization, and applications of lipases*", Biotechnology Advances, 2001, pp. 627-662, vol. 19, Elsevier Science Inc., Barking, GB.
Official Action issued on Mar. 28, 2008, in corresponding Chinese Patent Application No. 2005800005470 along with a partial English translation thereof, English transl. considered.
Office Action issued Nov. 15, 2010, in corresponding Japanese Patent Application No. 2006-519482.
Office Action issued on Jan. 19, 2011, in corresponding Taiwan Patent Application No. 094111250.
Office Action issued on Sep. 29, 2011, in corresponding Korean Patent Application No. 10-2006-7000995. translation provided by PTO considered.
Eugene Seitz, *Industrial Application of Microbial Lipases: A Review*, 51 Journal of the American Oil Chemists' Society 12-16 (Feb. 1974).

* cited by examiner

*Primary Examiner* — Susan Hanley
(74) *Attorney, Agent, or Firm* — Buchanan Ingersoll & Rooney PC

(57) ABSTRACT

A lipase powder which is a granulated substance containing a lipase and a solid content of animal milk, a lipase composition wherein said lipase powder is immersed or impregnated in fatty oil, and a method for producing the lipase powder which comprises the step of adding animal milk or cream derived from the animal milk to an aqueous solution containing a lipase, and the step of spray-drying, freeze-drying or solvent-precipitating the mixture thereof are provided. According to the present invention, a lipase powder of which lipase activity and stability are improved can be provided.

6 Claims, No Drawings

LIPASE POWDER, METHODS FOR PRODUCING THE SAME AND USE THEREOF

CROSS REFERENCE TO RELATED APPLICATION

The present application is a divisional application of U.S. patent application Ser. No. 11/320,756, filed Dec. 30, 2005, now abandoned, which, in turn, is a continuation of International Application No. PCT/JP05/06908, filed Apr. 8, 2005, which claims priority from Japanese Application No. 2004-114443, filed Apr. 8, 2004, the entire disclosure of each of which is incorporated herein by reference.

TECHNICAL FIELD OF THE INVENTION

The present invention relates to a lipase powder (powdered lipase) which can be appropriately used in the various esterification reactions such as a trans-esterification reaction; methods for producing the same; a lipase composition wherein the lipase powder is immersed or impregnated (or soaked) in fatty oil; a trans-esterification method of fatty oil, which comprises the step of using the lipase powder, and the like.

BACKGROUND OF THE INVENTION

Lipases are widely used in the reactions such as esterification of various carboxylic acids such as fatty acids with alcohols such as mono-alcohol and polyalcohol, and trans-esterification between plural carboxylates. In these, the trans-esterification method is an important technology not only as reforming animal and plant fatty oils but also as methods for producing various fatty esters, sugar esters and steroids. When a lipase, which is a fatty acid hydrolytic enzyme, is used as a catalyst of the above reactions, esterification can be conducted under the mild condition such as at room temperature to about 70° C. Therefore, the lipase can better inhibit side reactions and reduce energy costs compared with the existing chemical reactions. Besides those, a lipase as a catalyst is a natural product and, therefore, safe and secure. Further, the lipase can effectively produce the intended compounds through its substrate specificity and site specificity. However, even if lipase powder is used in esterification as itself, activity does not fully express. Further, it is difficult to uniformly disperse a lipase, which is basically a water-soluble product, into oily raw materials, and recover thereof is also difficult. Therefore, in the conventional methods, it is common to immobilize a lipase to some carriers, such as anion-exchange resin (Patent Literature 1), phenol adsorption resin (Patent Literature 2), a hydrophobic carrier (Patent Literature 3), cation-exchange resin (Patent Literature 4) and chelate resin (Patent Literature 5) and to use it in the reactions such as esterification and trans-esterification.

As mentioned above, a lipase has been conventionally immobilized and used in the esterification. However, the immobilized lipase loses an original lipase activity through the immobilization. In addition, when a porous carrier was used, the raw materials and products have gotten stuck in fine pores and, as a result, decreased the ester exchange ratio. Further, in the trans-esterification wherein the conventional immobilized lipase is used, water which a carrier retains is brought into the reaction system, and therefore, it has been difficult to prevent the side reactions such as production of diglyceride and monoglyceride in the trans-esterification of fatty oils.

In light of the situations mentioned above, various technologies have been developed wherein lipase powder is used. For example, a trans-esterification method is proposed wherein in the presence or absence of an inactive organic solvent(s), lipase powder is dispersed into a raw material(s) containing ester in the trans-esterification in such a manner that 90% or more of the particles of the dispersed lipase powder can keep particle size of 1 to 100 μm in the reaction (Patent Literature 6). It is also proposed that enzyme powder is used, which is obtained by drying an enzyme solution(s) containing phospholipid and lipid-soluble vitamins (Patent Literature 7).

However, there has been desired a lipase powder wherein the lipase activity and stability are further improved.

[Patent Literature 1] Japanese Patent Publication No. Sho 60-98984
[Patent Literature 2] Japanese Patent Publication No. Sho 61-202688
[Patent Literature 3] Japanese Patent Publication No. Hei 2-138986
[Patent Literature 4] Japanese Patent Publication No. Hei 3-61485
[Patent Literature 5] Japanese Patent Publication No. Hei 1-262795
[Patent Literature 6] Japanese Patent No. 2668187
[Patent Literature 7] Japanese Patent Publication No. 2000-106873

DISCLOSURE OF THE INVENTION

An object of the present invention is to provide a lipase powder wherein the lipase activity and stability are improved.

Another object of the present invention is to provide a lipase powder wherein the 1,3-selectivity of the lipase is improved.

Another object of the present invention is to provide lipase compositions wherein the lipase powder is immersed or impregnated in fatty oil.

A still another object of the present invention is to provide a method for producing the lipase powder.

A further object of the present invention is to provide a trans-esterification method of fatty oil, which comprises using the lipase powder.

The above objects and other objects will be apparent from the following descriptions.

Lipase activity and stability are extremely improved by granulating the lipase with a solid content of animal milk to obtain the powder thereof. In addition, in case where the lipase is a 1,3-specific lipase, the 1,3-selectivity is extremely improved. The present invention has been completed on the basis of these findings.

Namely, the present invention provides a lipase powder which is a granulated product containing a lipase and a solid content (solid material) of animal milk.

The present invention also provides a lipase composition wherein the lipase powder is immersed or impregnated in fatty oil.

The present invention further provides a method for producing a lipase powder which comprises adding animal milk or cream derived from animal milk to an aqueous solution containing a lipase, and spray-drying, freeze-drying or solvent-precipitating the mixture thereof.

The present invention further provides a lipase for trans-esterification or esterification containing the lipase powder.

The present invention further provides a trans-esterification method of fatty oil, which comprises using the lipase for the trans-esterification.

BEST MODE FOR CARRYING OUT THE INVENTION

The lipase used in the present invention includes a lipoprotein lipase, a monoacylglycerol lipase, a diacylglycerol lipase, a triacylglycerol lipase, a galactolipase, a phospholipase and the like. In these, the triacylglycerol lipase is preferred.

Microorganism which produces these lipases includes, without limited to bacteria, yeast, filamentous bacterium, *actinomyces* and the like, *Psudomonas* sp., *Alcaligenes* sp., *Arthrobacter* sp., *Staphylococcus* sp., *Torulopsis* sp., *Escherichia* sp., *Micotorula* sp., *Propionibacterum* sp., *Chromobacterum* sp., *Xanthomonas* sp., *Lactobacillus* sp., *Clostridium* sp., *Candida* sp., *Geotrichum* sp., *Sacchromycopsis* sp., *Nocardia* sp., *Fuzarium* sp., *Aspergillus* sp., *Penicillium* sp., *Mucor* sp., *Rhizopus* sp., *Phycomycese* sp., *Puccinia* sp., *Bacillus* sp., *Streptmycese* sp., *Thermomyces* sp. and the like.

In the present invention, in these, a 1,3-specific lipase is preferred; in particular, a 1,3-specific lipase derived from *Rhizomucor* sp. and *Alcaligenes* sp. is more preferred; and a 1,3-specific lipase derived from *Rhizomucor miehei* belonging to *Rhizomucor* sp., and *Alcaligenes* sp. is further preferred. Heretofore, *Rhizomucor miehei* sometimes used to belong to *Mucor* sp.

In the present invention, a 1,3-specific lipase derived from *Rhizopus* sp. and *Thermomyces* sp. is preferred; in particular, a 1,3-specific lipase derived from *Rhizopus oryzae* and *Thermomyces lanugenousus* is more preferred.

The animal milk used in the present invention includes cow milk, goat milk and the like. In these, the cow milk is preferred, in particular, the solid content of animal milk is preferably a solid content of cow milk or cream derived from cow milk.

Although the ratio of the lipase to the animal milk may be in various proportions, the solid content of animal milk is preferably 0.1 to 20 times, more preferably 1 to 20 times mass of lipase.

The lipase powder according to the present invention must comprise a lipase and a solid content of animal milk. The lipase powder may comprise, in addition to these components, a lipase culture component.

It is preferable that the lipase powder according to the present invention has a water content of 10% by weight or less, in particular, from 6.5 to 8.5% by weight.

Although the particle size of the lipase powder according to the present invention can be optional, it is preferable that 90% by weight or more of the lipase powder has the particle size of 1 to 100 μm. In this connection, it is preferable that an average particle size thereof be 20 to 80 μm, more preferably 20 to 50 μm. In addition, the lipase powder is preferably spherical.

The particle size of the lipase powder can be determined by, for example, Particle Size Distribution Analyzer (LA-500) of HORIBA, Ltd.

The lipase powder according to the present invention can be obtained by, for example, adding animal milk or cream derived from animal milk to an aqueous solution containing a lipase, and spray-drying, freeze-drying or solvent-precipitating the mixture thereof.

Examples of the solvent used in solvent-precipitation (precipitation with solvent) include ethanol, acetone, methanol, isopropyl alcohol and hexane, and a mixture thereof. Among these, ethanol and acetone are preferable since these solvents can further improve activity of lipase powder. The drying after solvent-precipitation can be conducted by, for example, drying under reduced pressure.

Here, examples of the aqueous solution containing a lipase include a lipase culture solution from which a cell body is removed, a purified culture solution thereof a solution in which the lipase powder obtained from these culture solutions is dissolved and dispersed again; a solution in which the commercially available lipase powder is dissolved and dispersed again; and a commercially available liquid lipase. In order to enhance lipase activity, it is more preferable that low-molecular-weight components such as salts are removed from the solution. In order to enhance the powder property, it is more preferable that low-molecular-weight components such as sugar are removed from the solution.

A lipase culture solution includes, for example, aqueous solutions containing soybean flour, peptone, corn steep liquor, $K_2HPO_4$, $(NH_4)_2SO_4$, $MgSO_4/7H_2O$ and the like. The concentrations thereof are as follows: the soybean flour is 0.1 to 20% by weight and preferably 1.0 to 10% by weight; peptone is 0.1 to 30% by weight and preferably 0.5 to 10% by weight; the corn steep liquor is 0.1 to 30% by weight and preferably 0.5 to 10% by weight; $K_2HPO_4$ is 0.01 to 20% by weight and preferably 0.1 to 5% by weight; $(NH_4)_2SO_4$ is 0.01 to 20% by weight and preferably 0.05 to 5% by weight; and $MgSO_4/7H_2O$ is 0.01 to 20% by weight and preferably 0.05 to 5% by weight. The culture conditions thereof should be controlled as follows: the culture temperature is 10 to 40° C. and preferably 20 to 35° C.; the quantity of airflow is 0.1 to 2.0 VVM and preferably 0.1 to 1.5 VVM; the rotation speed for stirring is 100 to 800 rpm and preferably 200 to 400 rpm; pH is 3.0 to 10.0 and preferably 4.0 to 9.5.

The separation of a cell body is preferably conducted by centrifugation, the membrane filter procedure and the like. The removal of the low-molecular-weight components such as salts and sugar can be treated with ultrafiltration membranes. Specifically, after the treatment with ultrafiltration membranes, the aqueous solution containing a lipase is concentrated so as to become ½ volume thereof, and then, the same amount of a phosphate buffer as that of the concentrated solution is added thereto. By repeating these procedures once to 5 times, the aqueous solution containing a lipase can be obtained, from which the low-molecular-weight components are removed.

The centrifugation is preferably controlled to 200 to 20,000×g. The pressure applied to the membrane filter is preferably controlled by microfiltration membranes, the filter press and the like to become not more than 3.0 kg/m². In case of enzymes in the cell body, it is preferable that cell breakage thereof is conducted by the homogenizer, Waring blender, the ultrasonic disruption, the French press, the ball mill and the like; then the cell residues are removed by centrifugation, the membrane filter procedure and the like. The rotation speed of the homogenizer for stirring is 500 to 30,000 rpm and preferably 1,000 to 15,000 rpm. The rotation speed of Waring blender is 500 to 10,000 rpm and preferably 1,000 to 5,000 rpm. The time for stirring is 0.5 to 10 minutes and preferably 1 to 5 minutes. It is preferable that the ultrasonic disruption is conducted under the condition of 1 to 50 KHz and more preferably 10 to 20 KHz. It is preferable that the ball mill has glass pellets having the diameter of 0.1 to 0.5 mm.

In the present invention, it is preferable that the aqueous solution containing a lipase is that containing 5 to 30% by weight of lipase as a solid content.

The solid content of the added animal milk or cream derived from animal milk is preferably 0.1 to 20 times, more preferably 0.3 to 10 times, most preferably 0.3 to 5 times mass of the solid content of the aqueous solution containing a lipase.

Here, the concentrations of the solid content in the aqueous solution containing a lipase and the solid content of the animal milk or the cream derived from animal milk can be determined as Brix. % by using, for example, the sugar content analyzer (Refractormeter) (CIS Corporation., Ltd.: BRX-242).

It is preferable that pH of the mixture of the aqueous solution containing a lipase and the animal milk or cream derived from animal milk is adjusted to the range of from 6 to 7.5 after the animal milk or cream derived from animal milk is added. In particular, pH is preferably adjusted to 7.0 or less, more preferably the range of from 6.5 to 7.0. Although it is preferable that pH adjusting is conducted immediately before the drying step such as spray-drying, pH adjusting can be conducted in any previous steps. It is possible that pH of the mixture is preliminarily adjusted in such a manner that pH immediately before the drying step is in the above-mentioned range. Although it is possible that various alkaline chemicals and acids are used in the step of adjusting pH, it is preferable to use an alkali metal hydroxide such as sodium hydroxide.

In some stage before the drying process, the aqueous solution containing a lipase may be concentrated. The concentration methods are not particularly limited and they include evaporator, flash evaporator, the concentration by ultrafiltration, the concentration by microfiltration, salting out by inorganic salts, precipitation methods with solvents, absorption methods with ion-exchange cellulose and the like, and water absorption methods with water-absorbing gels. Among these, the concentration by ultrafiltration and evaporator are preferable. The module for the concentration by ultrafiltration is preferably a flat membrane or a hollow fiber membrane having a fractioned molecular weight of 3,000 to 100,000 and more preferably 6,000 to 50,000. The materials of the membrane are preferably polyacrylonitrile, polysulfonic and the like.

It is preferable that spray drying is conducted by spray-dryers such as nozzle countercurrent flow, disk countercurrent flow, nozzle concurrent flow and disk concurrent flow, and the disk concurrent flow is more preferable. The spray-drying is preferably controlled as follows: the rotation speed of the atomizer is 4,000 to 20,000 rpm; and heating is 100 to 200° C. for inlet temperature and 40 to 100° C. for outlet temperature.

Freeze-drying is also preferable, for example, it is preferable that the freeze-drying is conducted by a tray stepwise type freeze-drying with a freeze-drying machine for small amount, which is laboratory size. Furthermore, the lipase powder can be prepared by drying under reduced pressure.

The lipase powder thus prepared can be used as itself. However, it is preferable, from the point of handling, that it is used as a lipase composition wherein the lipase powder is immersed or impregnated in fatty oil. Here, the mass of the fatty oil in the lipase composition is preferably 0.1 to 20 times and more preferably 1 to 20 times mass of the lipase powder.

The lipase composition can be easily obtained by adding the fatty oil to the lipase powder produced by spray-drying and the like; and then uniformly stirring the mixture by a stirrer, three-one motor, and the like. It can also be easily obtained by preliminarily adding the fatty oil to a powder recovering region of a spray-dryer; uniformly stirring the mixture after the recovering; and then removing the excess fatty oil by filtration.

The fatty oils for immersing or infiltrating the lipase powder are not particularly limited. They include vegetable oils such as canola oil, soybean oil, higholeic sunflower oil, olive oil, safflower oil, corn oil, palm oil and sesame-seed oil; triacylglycerols such as triolein (glycerol trioleate), tricaprilyn (glycerol trioctanoate), triacetin(glycerol triacetate) and tributyrin(glycerol tributyrate); and the mixture of one or more thereof such as fatty ester and sterol ester.

In case where the lipase is a 1,3-specific lipase, in particular, a lipase derived from *Rhizomucor miehei* and *Alcaligenes* sp., 1,3-selectivity of said lipase is extremely improved according to the present invention. Therefore, said lipase powder can be suitably used as a lipase for trans-esterification and for esterification. The trans-esterification of the fatty oil and the like, trans-esterification of the fatty oil and fatty acid ester, trans-esterification of alcoholysis and acidolysis, or esterification of glycerin and fatty acid can be effectively conducted by the ordinary method using the lipase powder.

The present invention provides a lipase powder having improved lipase activity and stability. In case where the lipase is a 1,3-specific lipase, 1,3-selectivity of a 1,3-specific lipase is extremely improved, and the fatty acid residue which is located on the second position of triglyceride as a raw material can be retained in the trans-esterification manufacture at an extremely high percentage.

The following Examples will further illustrate the present invention in detail.

Example 1

The low-molecular-weight components were removed by using the UF module (ASAHI KASEI CHEMICALS CORPORATION: SIP-0013) from a liquid lipase (Trade name: Palatase 20000L) of Novozymes Japan Ltd, in which a lipase derived from *Rhizomucor miehei* was dissolved and dispersed in an aqueous solution to obtain an aqueous solution 1 containing a lipase (the concentration of the solid content: 20.1% by weight). Specifically, liquid lipase (Palatase 20000L) was treated with ultrafiltration modules under cooling with ice and concentrated so as to become ½ volume thereof. Then, the same amount of a 0.01M phosphate buffer (pH 7) as that of the concentrated solution was added thereto. As for the obtained solution, the same procedures of ultrafiltration and the addition of a phosphate buffer were conducted twice and then, further ultrafiltration was conducted to obtain a lipase concentrated solution as the aqueous solution 1 containing a lipase.

To 20 ml of the aqueous solution 1 containing a lipase, 20 ml of cow milk (available from Koiwai Dairy Products Co. Ltd., "Koiwai Gyu-nyu Oishisa Shiate", the concentration of the solid content: 12.9% by weight) was added. The pH of the solution thus obtained was adjusted with an aqueous solution of sodium hydroxide to become the pH 6.8 to 6.9.

The volume ratio of the lipase concentrated solution (=the aqueous solution 1 containing a lipase) to the cow milk is 1:1. The solid content of the cow milk is 0.64 times mass of the solid content of the aqueous solution 1 containing a lipase.

Then, the solution was sprayed by using a spray-dryer (SD-1000: TOKYO RIKAKIKI Co., Ltd.) under the conditions of inlet temperature: 130° C., the air content for drying: 0.7 to 1.1 m$^3$/min, and spray pressure: 11 to 12 kpa to obtain lipase powder. The shape of the thus-obtained lipase powder was spherical, 90% by weight or more of the lipase powder has a particle size of 1 to 100 μm and the average particle size thereof was 7.6 μm. The particle size was determined by Particle Size Distribution Analyzer (LA-500) of HORIBA, Ltd.

The concentration of the solid content of the aqueous solution containing a lipase and the concentration of the solid content of the cow milk were determined by the following method.

The concentrations were determined as Brix. % by using the sugar content analyzer (Refractormeter) (CIS Corporation.: BRX-242).

Example 2

To the lipase concentrated solution obtained in Example 1, the same amount of water as that of the concentrated solution was added to obtain the aqueous solution 2 containing a lipase (The volume ratio of the lipase concentrated solution to water was 1:1). To obtain a lipase powder, the same procedure was conducted as that of Example 1 except that the aqueous solution 2 containing a lipase was used instead of the aqueous solution 1 containing a lipase. The volume ratio of the lipase concentrated solution:water:the milk was 0.5:0.5:1. The solid content of the cow milk was 1.05 times mass of the solid content of the aqueous solution (UF) containing a lipase.

Example 3

To the lipase concentrated solution obtained in Example 1, the same amount of 0.01M phosphate buffer (pH 7) as that of the concentrated solution was added to obtain the aqueous solution 3 containing a lipase (The volume ratio of the lipase concentrated solution to the buffer was 1:1). To obtain a lipase powder, the same procedure was conducted as that of Example 1 except that the aqueous solution 3 containing a lipase was used instead of the aqueous solution 1 containing a lipase. The volume ratio of the lipase concentrated solution:the phosphate buffer:the cow milk was 0.5:0.5:1. The solid content of the cow milk was 1.03 times mass of the solid content of the aqueous solution containing a lipase.

Example 4

To the lipase concentrated solution obtained in Example 1, the same amount of 0.01M phosphate buffer (pH 8) as that of the concentrated solution was added to obtain the aqueous solution 4 containing a lipase (The volume ratio of the lipase concentrated solution to the buffer was 1:1). To 20 ml of the aqueous solution 4 containing a lipase, 10 ml of cow milk (available from Koiwai Dairy Products Co. Ltd., "Koiwai Gyu-nyu Oisisa Shitate": the concentration of the solid content is 12.9% by weight) was added. The pH of the solution thus obtained was adjusted with an aqueous solution of sodium hydroxide to become the pH 6.8 to 6.9. The volume ratio of the lipase concentrated solution:the phosphate buffer: the cow milk was 0.5:0.5:0.5. The solid content of the cow milk was 0.52 times mass of the solid content of the aqueous solution containing a lipase.

Thereafter, a lipase powder was obtained as Example 1.

Example 5

To the lipase concentrated solution obtained in Example 1, the same amount of 0.01M phosphate buffer (pH 8) as that of the concentrated solution was added to obtain the aqueous solution 5 containing a lipase (The volume ratio of the lipase concentrated solution to the buffer was 1:1). To 20 ml of the aqueous solution 5 containing a lipase, 2 ml of cream fraiche (Trade name: Hokkaido Junsei Cream 35; available from Takanashi Milk Co. Ltd.; the concentration of the solid content is 43% by weight) was added. The pH of the solution thus obtained was adjusted with an aqueous solution of sodium hydroxide to become the pH 6.8 to 6.9.

The volume ratio of the lipase concentrated solution:the phosphate buffer:the cream fraiche was 0.5:0.5:0.1. The solid content of the cream fraiche was 0.34 times mass of the solid content of the aqueous solution containing a lipase.

Thereafter, a lipase powder was obtained as Example 1.

Example 6

To the lipase concentrated solution obtained in Example 1, the same amount of 0.01M phosphate buffer (pH 8) as that of the concentrated solution was added to obtain the aqueous solution 6 containing a lipase (The volume ratio of the lipase concentrated solution to the buffer was 1:1). To 20 ml of the aqueous solution 6 containing a lipase, 20 ml of Jersey cow milk ("Aso Shokoku Jersey 4.5 Milk"; available from Aso Agriculture Corporative Association; the concentration of the solid content was 13.2% by weight) was added. The pH of the solution thus obtained was adjusted with an aqueous solution of sodium hydroxide to become the pH 6.8 to 6.9.

The volume ratio of the lipase concentrated solution:the phosphate buffer:the cow milk was 0.5:0.5:1. The solid content of the milk was 1.06 times mass of the solid content of the aqueous solution containing a lipase. Thereafter, a lipase powder was obtained as Example 1.

Example 7

The same procedure was conducted as that of Example 1 except that freeze-drying was conducted as powdering means instead of spray-drying to obtain lipase powder. The freeze-drying was conducted as follows. An aqueous solution containing a lipase whose pH was adjusted to 6.8 to 6.9 was poured into a recovery flask and frozen by dry ice methanol. Then, the frozen material was freeze-dried by using a freeze-dryer (FDU-830) of TOKYO RIKAKIKAI CO, LTD at 0.15 Torr for 1 to 2 day(s). After drying, the resultant was lightly crushed in a mortar to obtain lipase powder.

Comparative Example 1

To obtain a lipase powder, the same procedure was conducted as that of Example 3 except that the cow milk was not added. The volume ratio of the lipase concentrated solution to the buffer was 1:1.

The activity of the lipase powder thus obtained was determined by the following method. The results were shown in Table 1.

Lipase Activity

To oil obtained by mixing triolein with tricaprilyn in the proportion of 1:1 (w), a lipase powder was added and then, the reaction thereof was conducted at 60° C. 10 μl of sample was taken with lapse of time, and diluted with 1.5 ml of hexane and then, a solution from which the lipase powder was filtered was obtained as a sample for gas chromatography analysis. The sample was analyzed by gas chromatography (column: DB-1 ht) to obtain the reaction rate thereof based on the following formulae. Conditions of the gas chromatography analysis were as follows: Column temperature: beginning 150° C., temperature rising 150° C./min., end 370° C.; other conditions were the same as those of the following determination of 1,3-selectivity.

$$\text{Reaction rate}(\%) = \{C34\ \text{area}/(C24\ \text{area}+C34\ \text{area})\} \times 100$$

Wherein "C24" denotes tricaprilyn, "C34" denotes tricaprilyn in which one fatty acid was substituted with C18, and "area" is area dimensions thereof.

The reaction rate constant K was determined from the reaction rates of each samples at each time by using the analysis software (orijin ver.6.1). The lipase activity was expressed as a relative value when K value of Comparative Example 1 was 100.

TABLE 1

| Condition (Volume Ratio) | Relative Activity |
|---|---|
| Comparative Example 1 Lipase concentrated solution:bf (7) = 1:1 | 100 |
| Example 1 Lipase concentrated solution:Cow Milk = 1:1 | 563 |
| Example 2 Lipase concentrated solution:Water:Cow Milk = 0.5:0.5:1 | 438 |
| Example 3 Lipase concentrated solution:bf (7):Cow Milk = 0.5:0.5:1 | 373 |
| Example 4 Lipase concentrated solution:bf (8):Cow Milk = 0.5:0.5:0.5 | 428 |
| Example 5 Lipase concentrated solution:bf (8):Cream = 0.5:0.5:0.1 | 355 |
| Example 6 Lipase concentrated solution:bf (8):Cow Milk = 0.5:0.5:1 | 435 |
| Example 7 Lipase concentrated solution:Cow Milk = 1:1 (freeze-dry) | 435 |

In the Table 1, "bf (7)" denotes 0.01M phosphate buffer (pH 7) and "bf (8)" denotes 0.01M phosphate buffer (pH 8). Except for Example 7, the spray-drying step was conducted.

It is clear from the results shown in Table 1 that the lipase activity is extremely improved according to the present invention.

1,3-selectivity of each Example 1, Example 7 and Comparative Example 1 was determined by the following method.
Determination of 1,3-Selectivity 1 mol of GRYCERYL-1,3-PALMITATE-2-OLEATE (POP) and 3 mol of OCTANOIC ETHYL(C8Et) were used as reaction substrates. Lipase powder was added thereto in such that the enzymatic activities become 0.5 to 5 w % of the substrates. The reaction was conducted at 60° C. and samples thereof were taken with lapse of time and diluted with hexane. The GC analysis was conducted to the samples, and the reaction rates of the 1.3 position (C16:0Et) and the second position (C18:1Et) were obtained by the following formulae.

$C16:0Et(\%) = \{C16:0Et \text{ area}/(C16Et+C18:1Et \text{ area}+C8Et \text{ area})\} \times 100$ $C18:1Et(\%) = \{C18:1Et \text{ area}/(C16Et+C18:1Et \text{ area}+C8Et \text{ area})\} \times 100$ The reaction rate constant K was determined from the reaction rates of each samples at each time by using the analysis software (orijin ver.6.1). At this time, the value of the final reaction rate is changeable. The reactivity of the 1.3 position was calculated when the reactivity of the second position was regarded as 1.
[GC Conditions]

| Column: | DB-1ht 5 m |
|---|---|
| Injection rate: | 1 μl |
| Carrier gas: | helium |
| Temperature in the vaporizing chamber: | 360° C. |
| Temperature of the detector: | 370° C. |
| Column temperature: | beginning 50° C., temperature rising 15° C./min, end 370° C. |

The results were shown in Table 2.

TABLE 2

| Condition (Volume Ratio) | 1,3-Selectivity |
|---|---|
| Comparative Example 1 Lipase concentrated solution:bf (7) = 1:1 | 20.8 |
| Example 1 Lipase concentrated solution:Cow Milk = 1:1 | 31.1 |
| Example 7 Lipase concentrated solution:Cow Milk = 1:1 (freeze-dry) | 22.7 |

From the result shown in Table 2, it is found that the 1,3-selectivity of the 1,3-specific lipase is extremely improved according to the present invention.

Stability of each lipase powder obtained by Example 1 and Comparative Example 1 was determined by the following method.
Stability Test Method The reaction using 5 g of tricaprilyn and 5 g of triolein was conducted at 60° C. for 24 to 72 hours. Initial decreasing levels of activity for each batch were plotted and the half-life period was calculated from total reaction time and the decreasing level of activity.

As a result, the half-life period of the lipase powder obtained by Example 1 was 913 hours and that of Comparative Example 1 was 234 hours. Therefore, the stability of the lipase powder according to the present invention was improved twice or more.

Example 8

A lipase powder of Meito Sangyo Co., Ltd. (Trade name: Lipase QL, derived from *Alcaligenes* sp.) was suspended in water to obtain an aqueous solution containing a lipase (the concentration of the solid content: 2.0% by weight). To 20 ml of the aqueous solution containing a lipase, 2 ml of cow milk (available from Koiwai Dairy Products Co. Ltd., "Koiwai Gyu-nyu Oishisa Shitate", the concentration of the solid content: 12.9% by weight) was added. The volume ratio of the aqueous solution containing a lipase to the cow milk was 10:1, and the solid content of the cow milk was 0.65 times mass of the solid content of the aqueous solution containing a lipase. The pH of the solution thus obtained was adjusted with an aqueous solution of sodium hydroxide to become the pH 6.8 to 6.9.

This solution was sprayed by using a spray-dryer (SD-1000: TOKYO RIKAKIKAI Co., Ltd.) under the conditions of inlet temperature: 130° C., the air content for drying: 0.7 to 1.1 m³/min, and spray pressure: 11 to 12 kpa to obtain a lipase powder. The shape of the thus-obtained lipase powder was spherical, 90% by weight or more of the lipase powder has a particle size of 1 to 100 μm and the average particle size thereof was 35 μm. The particle size was determined by Particle Size Distribution Analyzer (LA-500) of HORIBA, Ltd.

Comparative Example 2

To obtain a lipase powder, the same spray-drying procedure was conducted as that of Example 8 except that the cow milk was not added.

The lipase activity of these lipase powders was determined and expressed as a relative value when the activity of the lipase powder of Comparative Example 1 was 100. The results were, as a whole, shown in Table 3.

TABLE 3

| Condition (Volume Ratio) | 1,3-Selectivity |
|---|---|
| Comparative Example 2 Aqueous solution containing a lipase alone | 17.3 |

Example 8

Aqueous Solution Containing a Lipase:Cow Milk=10:1 31.1

From the results shown in table 3, it is clear that the lipase activity is improved about twice according to the present invention.

Example 9

The five times its amount of rape-seed oil was added to the lipase powder obtained in Example 1, the lipase powder was immersed in the rape-seed oil and an excessive amount of fat was removed by filtration to prepare a lipase composition containing a lipase powder/rape-seed oil in the proportion of 55/45% by weight.

Comparative Example 3

A (freeze-dried) powdery lipase (Lipase D "Amano") of Amano Enzyme Co., Ltd., which was derived from *Rhizopus oryzae* was re-suspended in water in 5% by mass concentration and the suspension was sprayed by using a spray-dryer (SD-1000: TOKYO RIKAKIKAI Co., Ltd.) under the conditions of inlet temperature: 130° C., the air content for drying: 0.7 to 1.1 m$^3$/min, and spray pressure: 11 to 12 kpa to obtain a lipase powder.

Example 10

The same (freeze-dried) powdery lipase (Lipase D "Amano") as that used in Comparative Example 3 was re-suspended in water in 5% by mass concentration, and to 5 ml of the lipase solution, 10 ml of cow milk (available from Meiji Dairies Co., Ltd., "Meiji Oishii Gyu-nyu", the concentration of the solid content: 12.9 mass %) was added. The resultant was sprayed by using a spray-dryer (SD-1000: TOKYO RIKAKIKAI Co., Ltd.) under the conditions of inlet temperature: 130° C., the air content for drying: 0.7 to 1.1 m$^3$/min, and spray pressure: 11 to 12 kpa to obtain a lipase powder.

Example 11

The same (freeze-dried) powdery lipase (Lipase D "Amano") as that used in Comparative Example 3 was re-suspended in water in 5% by mass concentration. To 5 ml of the lipase solution, 10 ml of cow milk (available from Meiji Dairies Co., Ltd., "Meiji Oishii Gyu-nyu", the concentration of the solid content: 12.9 mass %) was added. This lipase solution was stepwise added to 150 ml of ethanol preliminarily cooled to 0° C. or less to obtain the precipitate. The obtained precipitate was collected by a centrifuge machine (Beckman Co., Ltd.: GS-6KR) under the condition of 300 rpm for 10 minutes and then, the drying step was conducted under a reduced pressure by a dry machine (available from TOKYO RIKAKIKAI Co., Ltd.: FDU-830) for 16 to 20 hours to obtain a lipase powder.

The lipase activity of these lipase powders were determined to express as a relative value when activity of lipase powder of Comparative Example 3 was 100. The results were shown in Table 4.

TABLE 4

| | | Relative activity |
|---|---|---|
| Com. Example 3 | 5% lipase D → spray dry | 100 |
| Example 10 | 5% lipase D:cow milk = 1:2 → spray dry | 16360 |
| Example 11 | 5% lipase D:cow milk = 1:2 → ethanol-precipitation | 8420 |

From the results shown in Table 4, it is found that the lipase activity is extremely improved according to the present invention.

Comparative Example 4

A powdery lipase (Lipase F-AP15) of by Amano Enzyme Co., Ltd., which was derived from *Rhizopus oryzae* was re-suspended in water in 15% by mass concentration and the suspension was sprayed by using a spray-dryer (SD-1000: TOKYO RIKAKIKAI Co., Ltd.) under the conditions of inlet temperature: 130° C., the air content for drying: 0.7 to 1.1 m$^3$/min, and spray pressure: 11 to 12 kpa to obtain a lipase powder.

Example 12

The same lipase powder (Lipase F-AP15) as that used in Comparative Example 4 was re-suspended in water in 15% by weight concentration, and to 10 ml of the lipase solution, 10 ml of cow milk (available from Meiji Dairies Co., Ltd., "Meiji Oishii Gyu-nyu", the concentration of the solid content: 12.9 mass %) was added. The resultant was sprayed by using a spray-dryer (SD-1000: TOKYO RIKAKIKAI Co., Ltd.) under the conditions of inlet temperature: 130° C., the air content for drying: 0.7 to 1.1 m$^3$/min, and spray pressure: 11 to 12 kpa to obtain a lipase powder.

The lipase activity of these lipase powders was determined to express as a relative value when activity of lipase powder of Comparative Example 4 was 100. The results were shown in Table 5.

TABLE 5

| | | Relative activity |
|---|---|---|
| Com. Example 4: | 15% lipase F-AP15 → spray dry | 100 |
| Example 12: | 15% lipase F-AP15:cow milk = 1:1 → spray dry | 3700 |

From the results shown in Table 5, it is found that the lipase activity is extremely improved according to the present invention.

Comparative Example 5

A liquid lipase (Trade name: Lipozyme Tl 100L) of Novozymes Japan Ltd which was derived from *Thermomyces lanugenousus* was sprayed by using a spray-dryer (SD-1000: TOKYO RIKAKIKAI Co., Ltd.) under the conditions of inlet temperature: 130° C., the air content for drying: 0.7 to 1.1 m³/min, and spray pressure: 11 to 12 kpa to obtain a lipase powder.

Example 13

To the same liquid lipase (Trade name: Lipozyme Tl 100L) as that used in Comparative Example 5, 10 ml of cow milk (available from Meiji Dairies Co., Ltd., "Meiji Oishii Gyu-nyu", the concentration of the solid content: 12.9 mass %) was added. This lipase solution was sprayed by using a spray-dryer (SD-1000: TOKYO RIKAKIKAI Co., Ltd.) under the conditions of inlet temperature: 130° C., the air content for drying: 0.7 to 1.1 m³/min, and spray pressure: 11 to 12 kpa to obtain a lipase powder.

Comparative Example 6

10 ml of the same liquid lipase (Trade name: Lipozyme Tl 100L) as that used in Comparative Example 5 was stepwise added to 60 ml of ethanol preliminarily cooled to 0° C. or less to obtain the precipitate. The obtained precipitate was collected by a centrifuge machine (Beckman Co., Ltd.: GS-6KR) under the condition of 3000 rpm for 10 minutes and then, the drying step was conducted under a reduced pressure by a dry machine (available from TOKYO RIKAKIKAI Co., Ltd.: FDU-830) for 16 to 18 hours to obtain a lipase powder.

Example 14

To 1 ml of the same liquid lipase (Trade name: Lipozyme Tl 100L) as that used in Comparative Example 5, 10 ml of cow milk (available from Meiji Dairies Co., Ltd., "Meiji Oishii Gyu-nyu", the concentration of the solid content: 12.9 mass %) was added. This lipase solution was stepwise added to 60 ml of ethanol preliminarily cooled to 0° C. or less to obtain the precipitate. The obtained precipitate was collected by a centrifuge machine (Beckman Co., Ltd.: GS-6KR) under the condition of 3000 rpm for 3 minutes and then, the drying step was conducted under a reduced pressure by a dry machine (available from TOKYO RIKAKIKAI Co., Ltd.: FDU-830) for 16 to 20 hours to obtain a lipase powder.

The lipase activity of these lipase powders were determined to express as a relative value when activity of lipase powder of Comparative Example 5 was 100 The results were shown in Table 6.

TABLE 6

| | | Relative activity |
|---|---|---|
| Com. Example 5: | Tl 100L → spray dry | 100 |
| Example 13: | Tl 100L:cow milk = 1:10 (ml) → spray dry | 5200 |
| Com. Example 6: | Tl 100L → ethanol-precipitation | 0 |
| Example 14: | Tl 100L:cow milk = 1:10 (ml) → ethanol-precipitation | 8580 |

From the results shown in Table 6, it is found that the lipase activity is extremely improved according to the present invention.

What is claimed is:

1. A method for producing a lipase powder which comprises adding animal milk to an aqueous solution containing a lipase to obtain a mixture thereof, and spray-drying, freeze-drying, or solvent-precipitating the mixture thereof, wherein the solid content of the animal milk is 0.3 to 5 times the mass of the lipase and wherein the lipase is a lipase derived from *Rhizomucor* sp. or *Alcaligenes* sp.

2. The method according to claim 1, wherein the solid content of the added animal milk is 0.52 to 1.06 times the mass of the lipase.

3. The method according to claim 1 which further comprises adjusting the pH of the mixture to 6 to 7.5.

4. The method according to claim 1, wherein the aqueous solution containing a lipase is a lipase culture solution from which a cell body is removed, or a purified culture solution thereof.

5. The method according to claim 1, wherein spray-drying is conducted.

6. The method according to claim 5, which further comprises adjusting the pH of the mixture to 6 to 7.5.

* * * * *